United States Patent
Matonick

(10) Patent No.: US 8,230,717 B2
(45) Date of Patent: Jul. 31, 2012

(54) PARAVALVULAR LEAK TEST APPARATUS AND METHOD

(75) Inventor: John P. Matonick, Warren, NJ (US)

(73) Assignee: Ethicon, Inc., Somerville, NJ (US)

( * ) Notice: Subject to any disclaimer, the term of this patent is extended or adjusted under 35 U.S.C. 154(b) by 663 days.

(21) Appl. No.: 12/337,934

(22) Filed: Dec. 18, 2008

(65) Prior Publication Data

US 2010/0154507 A1    Jun. 24, 2010

(51) Int. Cl.
*G01L 27/00* (2006.01)
*G01M 3/04* (2006.01)
*A61F 2/06* (2006.01)

(52) U.S. Cl. .............. 73/1.72; 73/40; 623/912; 623/913

(58) Field of Classification Search .................. 73/1.72, 73/37, 40, 46, 168; 623/912, 913
See application file for complete search history.

(56) References Cited

U.S. PATENT DOCUMENTS

| | | | |
|---|---|---|---|
| 4,450,710 | A | 5/1984 | Nettekoven |
| 4,546,642 | A | 10/1985 | Swanson |
| 4,682,491 | A | 7/1987 | Pickard |
| 5,176,153 | A | 1/1993 | Eberhardt |
| 5,327,774 | A | 7/1994 | Nguyen et al. |
| 5,531,094 | A | 7/1996 | More et al. |
| 5,584,878 | A | 12/1996 | Love et al. |
| 5,899,937 | A * | 5/1999 | Goldstein et al. ............ 623/2.11 |
| 6,058,958 | A * | 5/2000 | Benkowski et al. ............ 137/14 |
| 6,062,075 | A | 5/2000 | Ritz et al. |
| 2003/0066338 | A1 | 4/2003 | Michalsky et al. |

FOREIGN PATENT DOCUMENTS

WO      2007/130987 A2    11/2007

* cited by examiner

*Primary Examiner* — Daniel Larkin
(74) *Attorney, Agent, or Firm* — E. Richard Skula

(57) ABSTRACT

An apparatus and method for measuring paravalvular leakage from a prosthetic heart valve in vitro. The apparatus has a pulse chamber pressure vessel and a pulsatile pump. The sewing ring of a prosthetic heart valve is mounted to a mounting member which is affixed to the pressure chamber, and paravalvular leakage from the heart valve is collected and measured.

21 Claims, 9 Drawing Sheets

PARAVALVULAR LEAK TEST APPARATUS AND METHOD

FIELD OF THE INVENTION

The field of art to which this invention relates is prosthetic heart valves, in particular, a method and apparatus for testing paravalvular leakage about a prosthetic heart valve.

BACKGROUND OF THE INVENTION

Prosthetic heart valves are well known in the art. The advent of the prosthetic heart valve has provided many patients with both improved quality of life and increased longevity. There are a variety of known conventional prosthetic heart valves available for use by the cardiac surgeon. Heart valves can be classified as mechanical or tissue (biological) valves. Examples of tissue valves include porcine heart valves, which are harvested intact and subsequently processed by glutaraldehyde in order to preserve the tissue valve. Other known tissue valves include those in which the leaflets are made from bovine pericardium, equine pericardium, and human pericardium.

Mechanical heart valves typically have a frame or structure containing the moveable elements (i.e. leaflets or occluder) that reproduce the function of the native or autologous leaflets of the heart valve. The main components of the valve structure, typically, consists of a valve ring which houses the leaflets and a sewing ring, which is the site of attachment of the valve to the native annulus. The leaflets of the mechanical valves may be made of conventional, biocompatible materials such as pyrolytic carbon, and are mounted in the valve ring by hinge points allowing hinged movement of the leaflets. The sewing ring of the valve provides an area for sutures or other means of fixation to mechanically attach the prosthetic valve to the annulus of the heart. The sewing ring is typically a synthetic polymeric woven structure that extends outward from the periphery of the prosthetic heart valve.

The primary function of a prosthetic heart valve is to act as a check valve, opening to permit antegrade blood flow and closing to prevent retrograde flow, about one hundred thousand times a day. The moveable elements move in response to a threshold pressure gradient in a direction allowing flow through the valve, while closing and preventing reverse flow below the threshold pressure gradient. The prosthetic heart valve simulates the function of a natural heart valve.

A heart valve replacement surgical procedure is typically performed in the following, conventional manner: The patient is placed on Cardiopulmonary Bypass (CPB) and their heart is arrested with the use of a cardioplegia solution. The flow of oxygenated blood is maintained throughout the systemic circulation, excluding the heart, through the use of conventional roller pumps on the CPB unit maintaining viability of the tissue. Surgical exposure of the diseased valve is then performed. The leaflets of the valve may be removed, as with the aortic valve, or secured back, as with the mitral valve. The native valve is then debrided of all visible signs of calcium. Sutures are placed around the annulus of the valve in either an everted or non-everted configuration, and the surgical needles that are mounted to the individual suture legs are secured to a suture management system. Once all the sutures have been placed around the annulus, the needles are then passed through the sewing ring of the valve and the valve is parachuted down to the annulus. The legs of the individual sutures are knotted with typically six to seven knots to ensure fixation of the valve.

Prosthetic heart valves go through extensive testing by the valve manufacturer to ensure the durability of the device, the fluid flow characteristics, and the leakage through the valve orifice with the leaflets in the closed position. Failure of the prosthetic heart valves in vivo can have catastrophic results. However, the manufacturer's focus of the tests is with respect to the valve functionality and not the fixation or attachment of the valve to the annulus of the heart of the patient.

One of the critical parameters of a successful valve replacement procedure is attaching the valve to the native annulus and creating a seal between the valve sewing ring and annular tissue that eliminates the leakage of blood between the two. This type of leakage is referred to as paravalvular leakage. Paravalvular leakage is defined as the flow of blood from one side of the valve to the other, while the valve is closed through regions other then through the orifice of the valve (i.e., through the sewing ring, under the sewing ring, and alongside the suture). The assessment of paravalvular leakage has historically been performed either in vitro in a bench top pulse duplicator system or in vivo in acute or chronic animal studies, using indirect methods of analysis, such as color flow Doppler ultrasound imaging or the transvalvular pressure tracings to assess a valve fixation device or technique. The effects of paravalvular leakage upon the post operative valve transplant patient include: hemolysis, hemodynamic instability, dehiscence, or valvular dysfunction.

There are disadvantages associated with these historical methods. Ultrasound color flow Doppler imaging algorithms yield a high degree of random and systematic error when assessing a 3-dimensional structure with multidirectional flow regions. Transvalvular pressure measurements, throughout the cardiac cycle, have also been used to attempt to evaluate the degree of paravalvular leakage, however, isolating alterations in the transvalvular pressure tracing to a paravalvular leakage is inaccurate and unquantifiable. The methods used to date involve indirect measurements of leakage from regions of the valve structure that is fully contained within the natural flow field (i.e. aorta or left atrium). None of these techniques provide a true quantifiable means of the absolute measurement of paravalvular leakage.

While existing methods of valve testing apply only to the evaluation of the valve leaflet function, there is an unmet and pressing need for a novel apparatus and in vitro method for evaluation of the integrity of valve fixation and the measurement of paravalvular leakage.

SUMMARY OF THE INVENTION

Accordingly, an apparatus for in vitro testing of prosthetic heart valves for paravalvular leakage is disclosed. The apparatus has a pulse chamber pressure vessel, which has a top, a bottom, at least one side, an interior volume, an inlet and an outlet. There is at least one valve mounting opening in the bottom of the pulse chamber pressure vessel in fluid communication with the interior volume. A flexible, annular valve mounting member is mounted about each valve mounting opening for mounting a sewing ring of a prosthetic heart valve thereto. An additional fixture is preferably provided to restrain the moveable members of the heart valve and to block the flow of fluid through the orifice of the valve. The testing apparatus has a pulsatile pump having an inlet and an outlet. The pump outlet is fluidly connected to the inlet of the pulse chamber vessel. There is a drip collection chamber vessel having an inlet and an outlet, located beneath the pulse chamber. The drip collection vessel is in fluid communication with each heart valve to collect paravalvular leakage from the heart valve, which can then be measured.

Another aspect of the present invention is a method of testing a prosthetic heart valve for paravalvular leakage using the previously described testing apparatus.

DETAILED DESCRIPTION

Figure 1A:
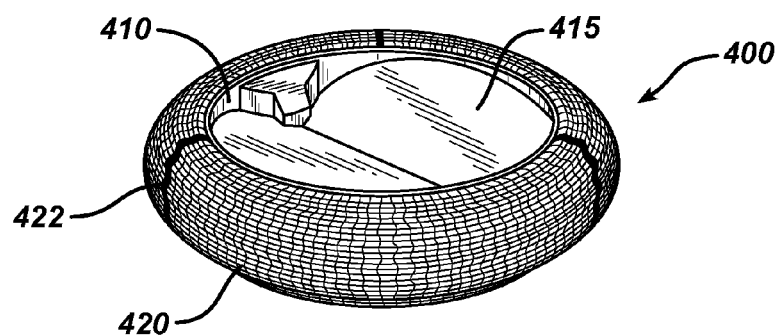
FIG. 1A is a perspective view of a synthetic, prosthetic heart valve.
Figure 1B:
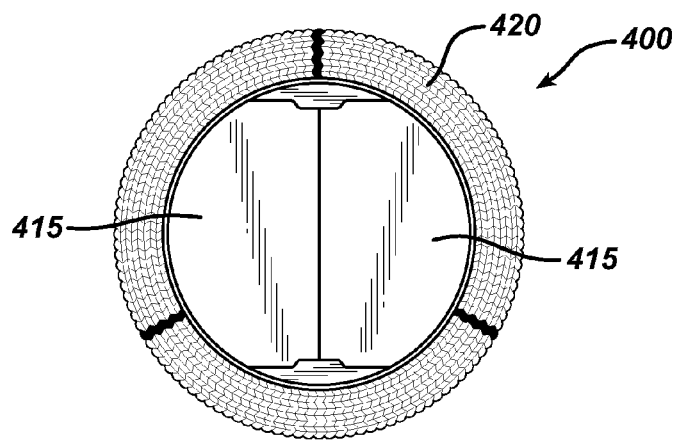
FIG. 1B is a top view of the prosthetic heart valve of FIG. 1A.
Figure 1C:
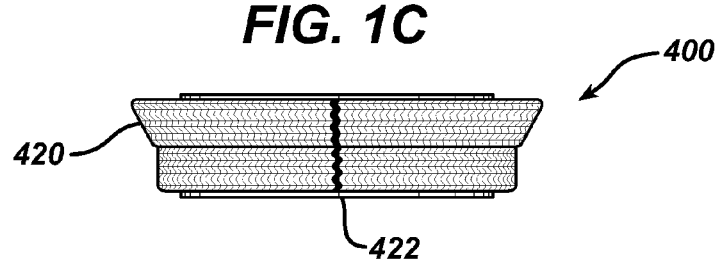
FIG. 1C is a side view of the prosthetic heart valve of FIG. 1A.
Figure 1D:
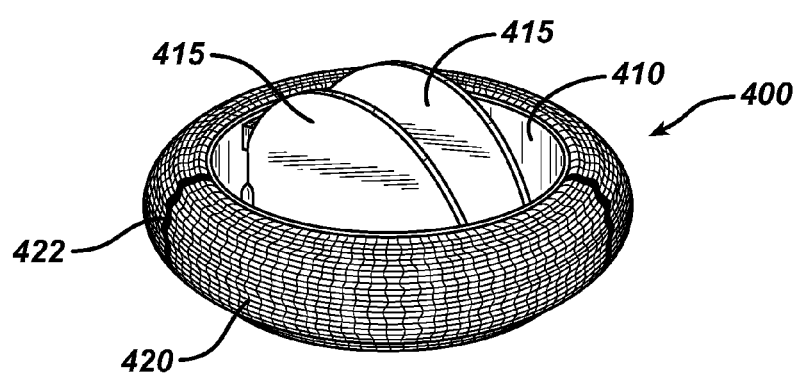
FIG. 1D is a perspective view of the prosthetic heart valve of FIG. 1A with the leaflettes in the open position.

Referring first to FIGS. 1A-D, a conventional prosthetic, synthetic heart valve 410 is illustrated. The valves 400 are seen to have frames 400 and hinged leaflettes 415 mounted therein. Mounted about the frame 410 is the sewing ring 420. Sewing ring 420 is made from a conventional biocompatible synthetic fabric having sufficient strength to effectively affix a valve frame 410 to a valve annulus using surgical needles and sutures. Seen on the sewing rings 420 are the locating lines 422 to assist the surgeon in positioning the valve in a valve annulus.

Figure 2A:
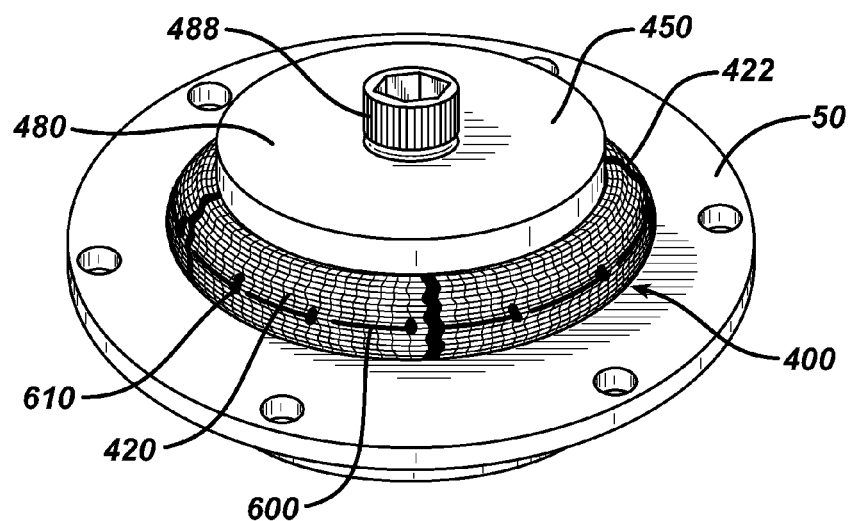
FIG. 2A is a perspective view of a bottom of a fixture mounted to a pulse chamber for holding a prosthetic heart valve during paravalvular testing and having a prosthetic heart valve contained therein mounted to the a mounting ring on the bottom of the chamber.
Figure 2B:
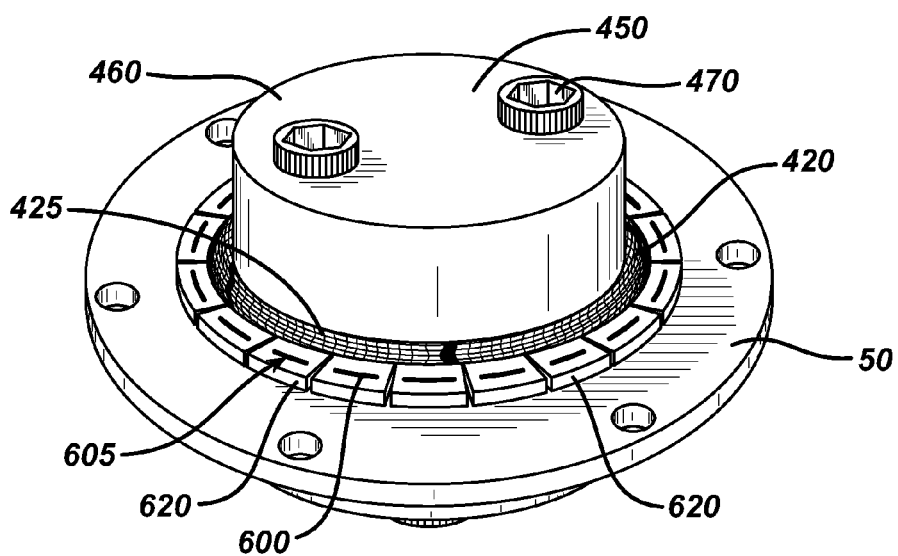
FIG. 2B is a perspective view of the top of the fixture of FIG. 2A mounted to the pulse chamber.
Figure 3:
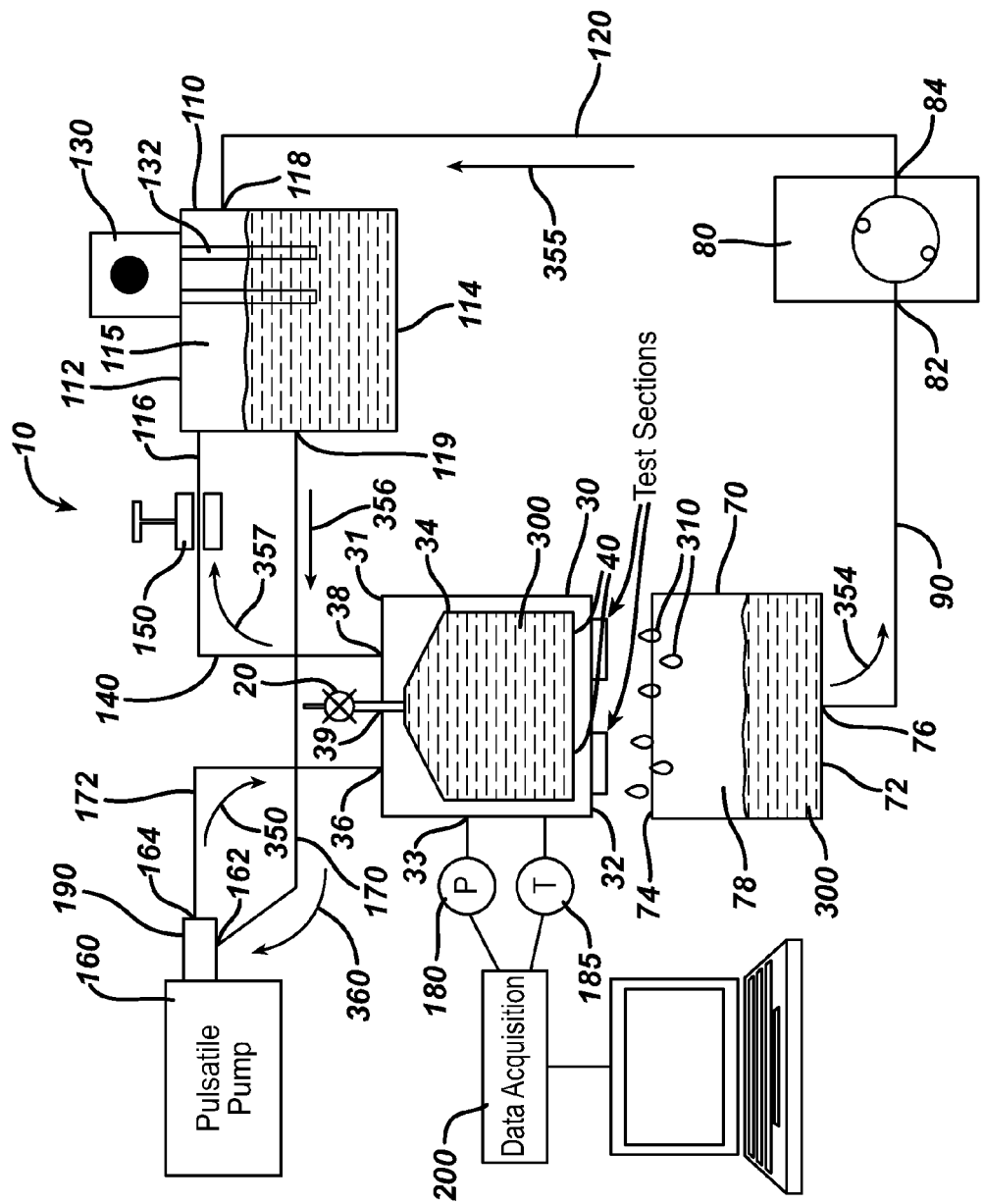
FIG. 3. is an illustration of a schematic of a paravalvular leak test apparatus of the present invention and a flow diagram.
Figure 4:
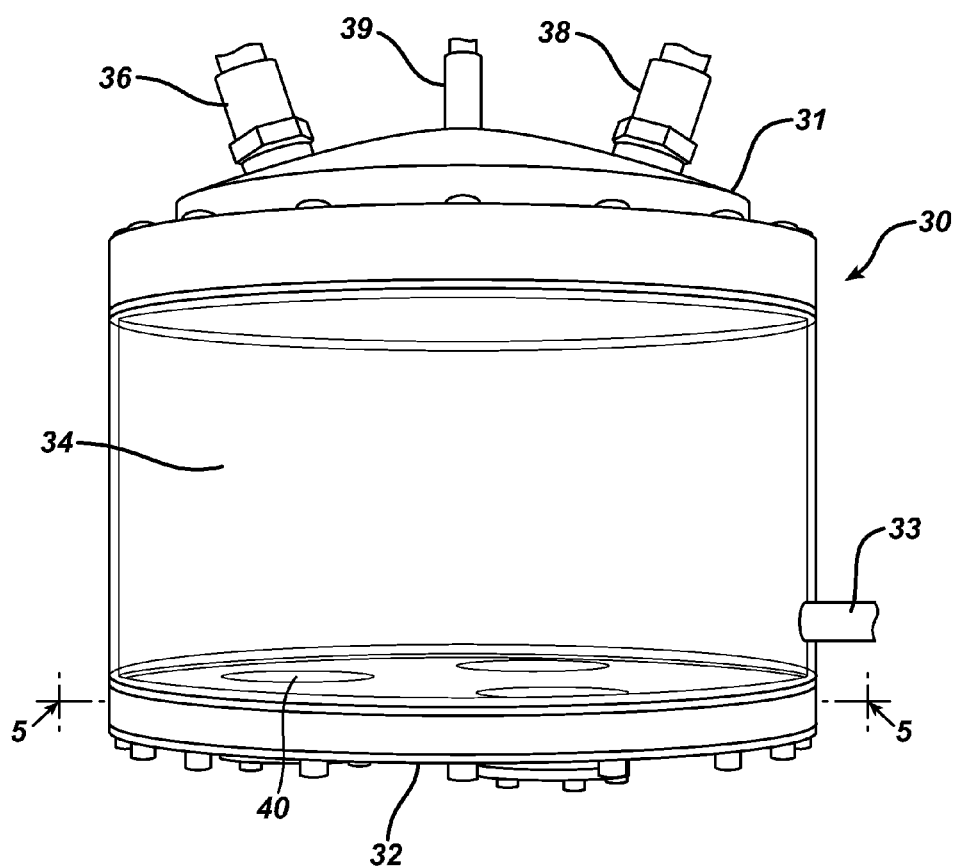
FIG. 4 is an illustration of a pulse chamber, useful in the apparatus of the present invention.
Figure 5:
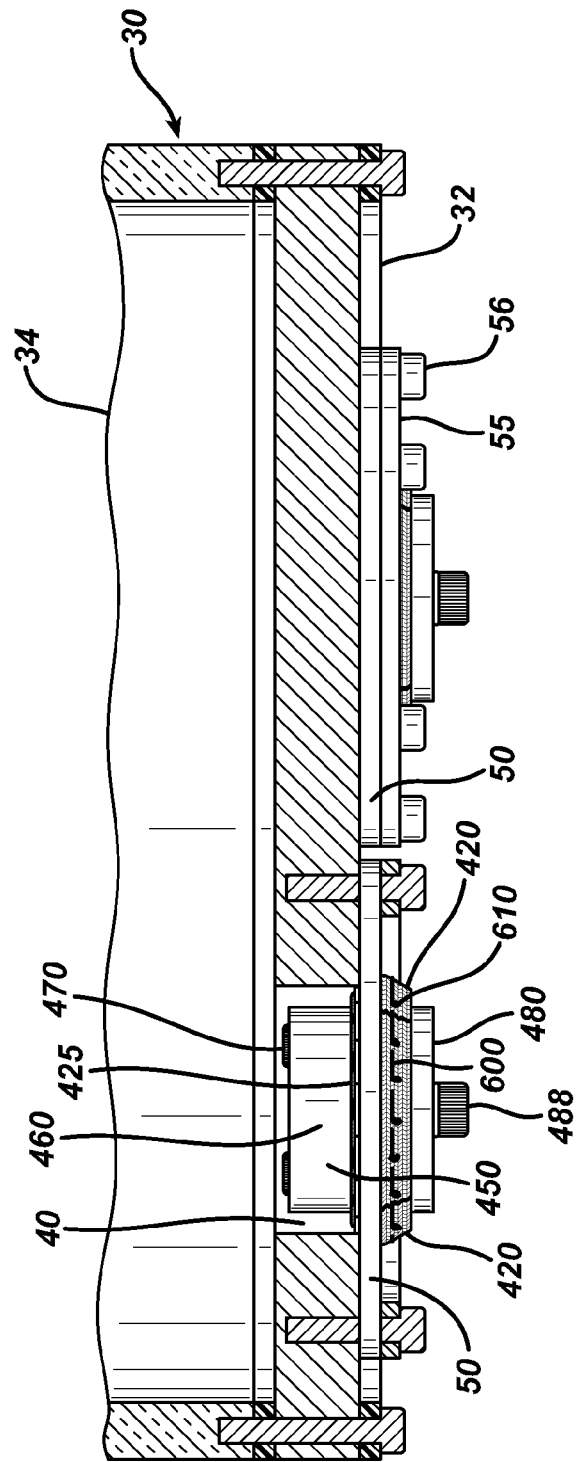
FIG. 5 is a partial cross-section of the pulse chamber of FIG. 4 along View line 5-5, illustrating valves mounted to the bottom of the pulse chamber.
Figure 6:
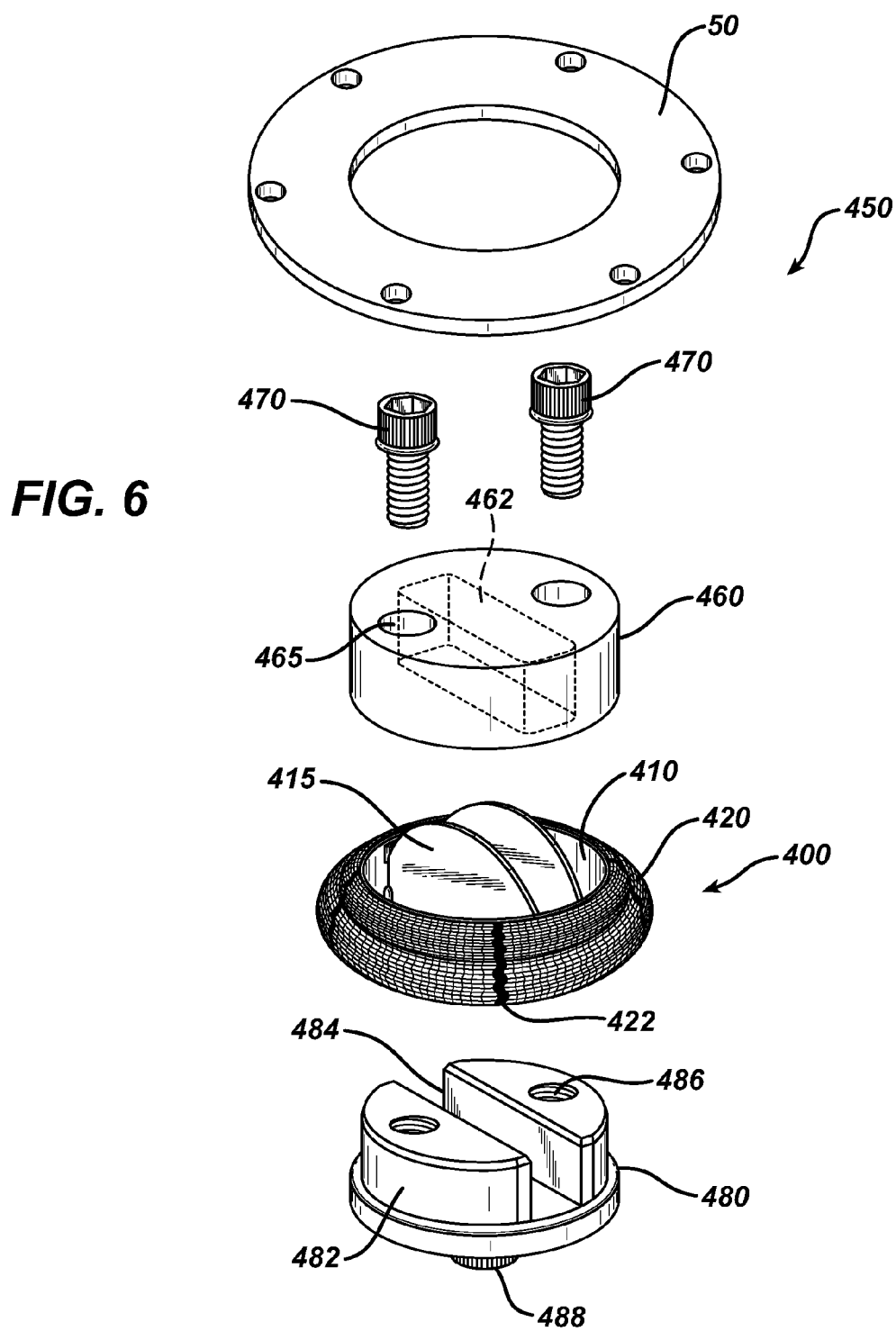
FIG. 6 is an exploded perspective view of a prosthetic heart valve, a fixture and a mounting ring used to mount a prosthetic heart valve to the paravalvular leak test apparatus of the present invention.
Figure 7:
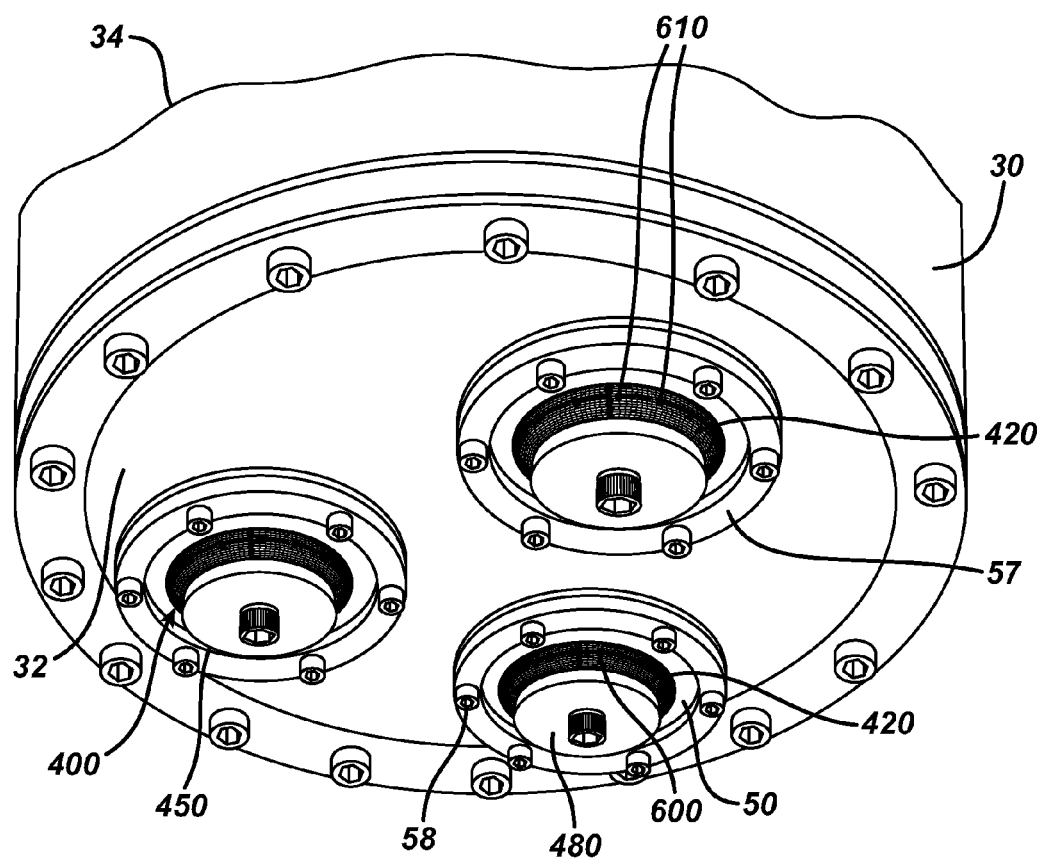
FIG. 7 is a partial perspective view of the pulse chamber of FIG. 4, showing the bottom of the pulse chamber.

The paravalvular leak tester or apparatus 10 of the present invention is illustrated in schematic form in FIG. 3. The apparatus 10 is seen to have pulse chamber 30. Pulse chamber 30 is also illustrated in FIGS. 4, 5 and 7. Pulse chamber 30 is a pressure vessel having a top 31, a bottom 32, an interior volume or space 34, a top inlet 36, a top outlet 38, and a vent outlet 39. Vent outlet 39 is seen to be connected to conventional stopcock 20, which is in turn vented to atmosphere. If desired, a conventional pressure relief valve may be mounted to pulse chamber 30 to prevent an over-pressure condition from occurring. Outlet 33 for receiving a pressure transducer is also seen to extend from the side of chamber 30. In the bottom 32 of pulse chamber 30 are the mounting openings 40 that extend into the interior 34. Surrounding each opening 40 is a mounting member 50 as shown in FIG. 5. Mounting members 50 are mounted to the bottom 32 of chamber 30 in a conventional fluid tight manner such as by compressing the valve mounting substrate against the bottom of the pulse chamber. A prosthetic heart valve 400 is seen to be mounted in each opening 40. The heart valves 400 are mounted to the openings 40 as seen in FIGS. 2A and 2B. The heart valves 400 are each mounted in a mounting fixture 450 prior to mounting in openings 40 in the bottom 32 of chamber 30. Also referring to FIGS. 2A, 2B and 6, each valve 400 is mounted in a fixture 450 such that the peripheral sewing ring of the valve 400 extends beyond the outer periphery of the mounting fixture 450. Each heart valve 400 is mounted to flexible mounting member 50 with the method of valve fixation or attachment against which the paravalvular leakage is to be measured. The mounting members 50 are ring members having a central annular opening 55 for receiving a heart valve 400 mounted to a fixture 450. The member 50 will be flexible and capable of having sutures passed therethrough without allowing leakage about the suture and will be generally capable of providing a fluid tight seal when mounted in openings 40. The member 50 is seen to be mounted with flanges 57 and bolts 58, as shown in FIG. 7, but may be mounted to bottom 32 about openings 40 in other conventional manners including gluing, welding, cementing, etc. In a preferred mounting method, the sewing ring is attached to mounting member 50 using a plurality of surgical sutures using conventional techniques.

The mounting fixture 450 is seen to have bottom section 480 and top section 460 having leaflette receiving cavity 462, and bolt openings 465. Bottom 480 is seen to have a pair of opposed leaflet retention members 482 separated by space 484, threaded bolt holes 486 and bottom knob 488. Valve 400 is mounted in fixture 450 by rotating the valve leaflettes 415 upward, and placing ring and frame around members 482 and then mounting top 460 to bottom 480 such that leaflettes 415 are contained in cavity 462 and space 484. The top and bottom sections 460 and 480 are then secured by bolts 470. Situated beneath and in alignment with the bottom 32 of pulse chamber 30 is the collection drip chamber 70. Drip Chamber 70 is a vessel having a bottom 72 and an open top 74, as well as interior volume or space 78. Although preferred that top 74 be open, the chamber 70 may have a closed top with openings into which paravalvular leakage is channeled. In an alternate embodiment, drip chamber 70 may have separate compartments correspondingly located beneath each valve 400. Drip Chamber 70 is seen to have bottom outlet 76. The outlet 76 is seen to be connected to inlet 82 of pump 80 by tubing or pipe member 90. Pump 80 also has outlet 84. Pump 80 may be any type of conventional pump such as a roller pump, piston pump, or centrifugal pump. It is particularly preferred that pump 80 be a roller pump. Fluid reservoir 110 is seen to be a vessel having top 112 and bottom 114, and interior volume or space 115. Reservoir 110 is seen to have first inlet 118 and outlet 119. The discharge outlet 84 of pump 80 is connected to first inlet 118 by tubing 120. The terms tubing, piping, tube, pipe, and fluid conduit are used interchangeably herein. Fluid reservoir 110 is seen to have heater 130 mounted thereto. Heater 130 has heating elements 132 extending into the interior volume 115. Heater 130 may be any type of conventional heater including circulating heaters, and submersible heaters. Heater 130 will have conventional controls to maintain a constant fluid temperature, such as a thermostat, thermocouple, or thermistor sensor feedback for constant temperature regulation. Second outlet 38 of pulse chamber 30 is connected to the inlet 116 of fluid reservoir 110 by tubing 140. Tubing 140 is also seen to have impedance control valve 150 mounted thereto. Impedance control valve 150 may be a conventional valve such as an adjustable tubing clamp, a gate valve, a ball valve, etc. The outlet 119 of fluid reservoir 110 is seen to be connected to the inlet 162 of pulsatile pump 160 by tubing 170. Pulsatile pump 160 is seen to also have discharge outlet 164. Pulsatile pump 160 is a conventional pump, such as a piston pump. Pump 160 is capable of providing a constant stroke volume of fluid creating a cyclical pressure wave consistent with the pressure waveforms against which the prosthetic heart valves 400 must function. Pump 160 has standard controls which allow the pulse rate and stroke volume to be controlled. The discharge pressure of pump 160 and pulse chamber waveform is controlled through a combination of the stroke volume, pulse rate, and impedance control valve. The discharge 164 of pump 160 is fluidly connected to the top inlet 36 of pulse chamber 30 by fluid conduit 190. Mounted to pulse chamber 30 and extending into the interior are the conventional pressure transducer 180 and the conventional temperature transducer 185. Pressure transducer 180 may be any pressure transducer and equivalents thereof, such as fluid coupled or solid-state transducers. Temperature transducer 185 may be any conventional temperature transducer and equivalents thereof, such as a thermistor or thermocouple sensor. The transducers 180 and 185 are connected to data acquisition computer 200 in a conventional manner. Data acquisition computer 200 is a conventional analog to digital convertor with digital storage capability and real time signal presentation. Computer 200 functions in the following manner. The pressure and temperature sensor analog voltage signals from sensors 180 and 185 are converted into digital values at a preset sample rate, displayed on the monitor, and stored in a data file for future signal processing and presentation.

Figure 3A:
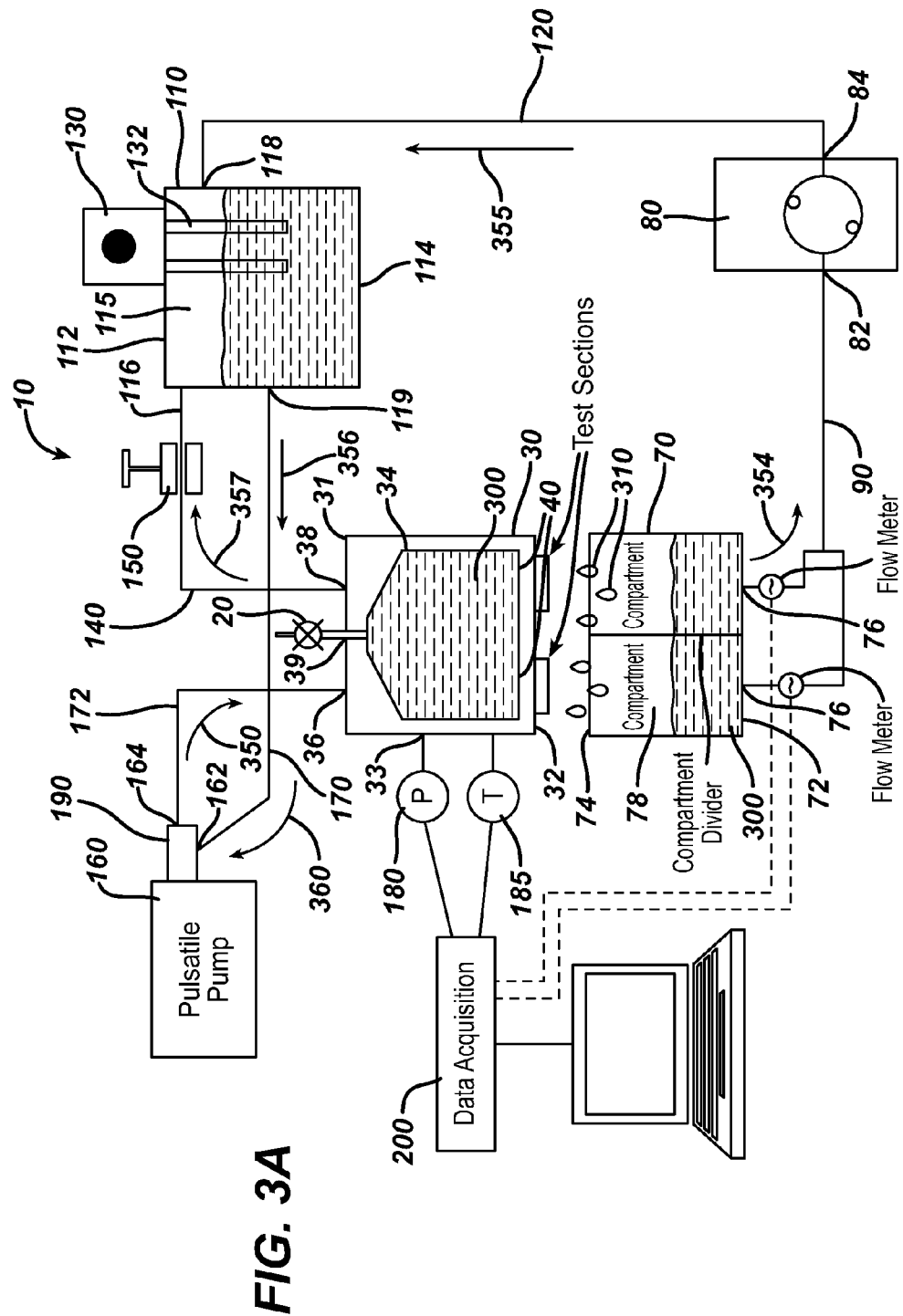
FIG. 3A is an illustration of a schematic of a paravalvular leak test apparatus of the present invention and a flow diagram according to an alternative embodiment.

The paravalvular leak test apparatus of the present invention is used to test prosthetic heart valves for paravalvular leakage in the following manner. Initially, one or more prosthetic heart valves 400 are mounted to mounting fixtures 450 such that the valve leaflets 415 are constrained from moving, and the sewing ring 420 is contained between sections 460 and 480 of mounting fixture 450. Valve 400 constrained within mounting fixture 450 is mounted to pulse chamber 30 by inserting the valve 400 and fixture 450 into opening 55 in mounting members 50 on the bottom 32 pulse chamber 30. The sewing ring of the valve 400 is mounted to the mounting member 50 in a conventional manner, such as by suturing with a plurality of conventional sutures, in accordance with conventionally known valve mounting techniques. As shown in FIGS. 2A, 2B, 5 and 7, conventional sutures 600 are passed through rings 420 using conventional surgical needles and knotted on one side of ring 420 with knots 610. The sutures 600 also have conventional pledget members 620 conventionally mounted to central sections 605. The pledget members are contained on the top 425 of ring 420, while the knots 610 are on the bottom 427. Such techniques provide relatively fluid-tight mounting. If desired, the sewing ring 50 may be mounted using other fastening devices including staples, barbed sutures, etc., and may also be mounted using biocompatible glues. Next, after the sewing rings of the valves 400 have been securely affixed to mounting members 50, the fixtures 450 and rings 50 are mounted to the openings 40 using flanges 57 and bolts 58. —The pulse chamber 30 and fluid reservoir 110 are filled with a sufficiently effective amount of a fluid 300. The fluid 300 may be water, distilled water, blood analogue (e.g., glycerol and water), plasma, blood, etc. It is important that the interior cavity 34 of pulse chamber 30 be completely filled with the fluid 300 and that substantially all gas is vented off or out from the interior volume 34. Next, the stroke volume and pulse rate of pulsatile pump 160 are set to simulate a typical human pulse rate, blood flow rate and pressure. The settings will typically range from about 20 ml to about 60 ml for stroke volume, about sixty cycles per minute to about eighty cycles per minute for pulse rate, and about 120/10 mmHg for pressure. The pulse pressure and pressure waveform is established through an adjustment of the stroke volume and pulse rate of the pump and an adjustment of the impedance control. However, an infinite number of combinations of stroke volume, pulse rate, and pressure may be created to evaluate the paravalvular leakage of a prosthetic heart valve for different physiological conditions and pathologies, such as enhanced contractility, hypertension, and tachycardia. Once flow of fluid 300 through pump 160 has been initiated, and a steady state pressure and temperature have been achieved and maintained via input from transducers 180 and 185 and computer 200, the apparatus 10 is allowed to cycle and run, while paravalvular leakage 310 is collected in drip chamber 70. The leakage 310 may be measured manually in the following manner. An empty collection vessel of adequate size is placed on a scale and the scale tared. The collection vessel is then positioned beneath the valve 400 being tested and the droplets collected for a period of time, such as one or two minutes. The collection with the paravalvular a leakage fluid is placed on the scale and the weight is converted to leakage rate based on the density of the fluid. The collected fluid 300 is then returned to fluid reservoir 110. In an alternate embodiment, as shown in FIG. 3A, drip chamber 70 is compartmentalized into chambers such that there is a separate chamber beneath each heart valve 400.

Leakage from each heart valve is accordingly directed to a separate chamber. The flow from each individual chamber is measured by a conventional flow meter prior to exiting chamber 70 at bottom outlet 76. The flow rates are then sent via an electrical signal to computer 200, where the data is stored and also displayed as a real time flow or leakage rate for each valve 400.

Pump 80 is simultaneously actuated at the initiation of the test. Pump 80 then pumps fluid 300 from the drip chamber 70 to fluid reservoir 110.

In operation, the paravalvular test apparatus of the present invention operates in the following manner. The pulsatile pump 160 directs fluid 300 in the direction of arrow 350 through pipe 190 and through inlet 36 into the interior volume 34 of pulse chamber 30. The fluid flows in a pulsatile fashion corresponding to the stroke volume, rate and discharge pressure of pump 160. Fluid 300 flows out of chamber 30 either as a paravalvular leakage component 310 of fluid 300, about or through the sewing rings 420 of valves 400 into drip chamber 70, or as fluid 300 out through outlet 38 through pipe 140 to fluid reservoir 110. The total flow from pump 160 into pulse chamber 30 will be equal to the sum of the paravalvular leakage 310 plus the discharge flow out through outlet 38. While residing in fluid reservoir 110, the fluid 300 is heated by the elements 132 of heater 130 to the desired temperature. Fluid 300 consisting of paravalvular leakage 310 is manually measured by weighing the timed volume of fluid collected in a container. Alternatively, drip chamber 70 has separate compartments aligned such that the paravalvular leakage 310 from each valve 400 is collected in a separate chamber. The flow from each chamber is then measured by a conventional flow meter, which sends data to computer 200 for collection and display. The paravalvular leakage 310 is then collectively or individually routed to discharge 76 for movement to pump 80. Fluid 310 moves through pipe 90 in direction 354 to inlet 82 of pump 80. The paravalvular leakage 310 is returned to fluid reservoir 110 by exiting the discharge port of the discharge pump 80, which pumps the paravalvular leakage 310 in the direction of arrow 355 through conduit 120 to fluid reservoir 110 where it is commingled with fluid 300. Discharge pump 110 may be set to operate continuously or to start and stop periodically in correspondence to fluid 310 levels in drip chamber 70. During operation, fluid will also flow from pulse chamber 30 through conduit 140 in the direction of arrow 357 to fluid reservoir 110. Fluid 300 is seen to move from fluid reservoir 110 through conduit 170 in the direction of arrow 356 to the inlet 162 of pulsatile pump 160. The pressure waveforms and temperature of the fluid are monitored continuously by computer 200 through the input signals from the pressure and temperature sensors.

During operation, leak test apparatus 10 acquires and records the following data via computer 200: pulse chamber pressure and pulse chamber temperature, and optionally paravalvular leakage 310.

The following example is illustrative of the principles and practice of the present invention, although not limited thereto.

Example

Paravalvular Leak Testing

Three synthetic prosthetic heart valves were tested for paravascular leakage using the apparatus and test method of the present invention. The heart valves were 33 mm mechanical bi-leaflet mitral valves, standard open-pivot design, manufactured by ATS Medical. The valves were mounted to the pulse chamber of the device of the present invention by mounting the sewing rings of the valves to the mounting members of the pulse chamber, and then mounting the valves in a fixture to constrain the leaflettes. This was done using Ethicon Ethibond EXCEL* (2-0) sutures. Each valve was mounted to a mounting member in the following manner:

A valve orifice, of the appropriate diameter was cut out of ⅛" silicone to accept the valve, Ethibond EXCEL* sutures were then placed in a horizontal mattress non-everted configuration, and the sutures knotted with seven throws each. The apparatus was prepared for testing by filling the system with a fluid consisting of distilled water and starting the pulsatile pump. Air was vented from the pulse chamber to ensure that the pulse chamber was completely filled with fluid. The pulsatile pump was set to have a stroke volume of approximately 35 ml and a pulsed or cyclical rate of approximately seventy two strokes per minute. Once the drip chamber had collected a sufficient volume of fluid, a pump connected to the outlet of the drip chamber was started to pump the fluid in the collection chamber to the fluid reservoir. The temperature controls on the heater in the fluid reservoir were set to maintain a temperature of approximately 37° C. During the course of the testing, paravalvular leakage was manually measured by collecting paravalvular leakage by placing a container beneath each valve for a period of time equal to two minutes. The test was run for 48 hrs or approximately 200,000 cycles during which temperature and pressure were continually monitored. A summary of the data collected is presented in Table 1.

Table 1.
Paravalvular Leak Rate Data

The paravascular heart valve testing apparatus and method of the present invention have many advantages. The advantages include the following. The paravalvular leak tester provides a means of absolute measurement of paravalvular leakage of a valve fixation device or technique in a static or dynamic pulsed environment. The tester provides for direct visualization of the valve, fluid loss, and performance of the device. The system is independent of the configuration of the valve/substrate design, allowing infinite choices of substrate materials, substrate configurations, sewing ring fabrics, valve designs, and methods of fixation. Examination of the valve fixation device or technique is possible over a broad range of pressures and pulse rates covering all physiological conditions (i.e. hypertension,

| Time (hours) | Leak Volume (ml) | Accumulated number of pulses | Leak rate per pulse |
|---|---|---|---|
| 0 | 205 | 0 | 2.85 |
| 4 | 193 | 17,280 | 2.68 |
| 22 | 110 | 95,040 | 1.53 |
| 44 | 62 | 190,080 | 0.86 |
| 52 | 51 | 224,640 | 0.71 |
| 67 | 42 | 289,440 | 0.58 |
| 78 | 38 | 336,960 | 0.53 |
| 92 | 28 | 397,440 | 0.39 |
| 101 | 24 | 436,320 | 0.33 |
| 117 | 20 | 505,440 | 0.28 | hypotension, bradycardia, tachycardia) as well as values far beyond life sustainable limits to examine forces required to take the fixation to failure. The design of the system allows for continual un-monitored operation, twenty-four hours a day, seven days a week. The system remains undisturbed during the actual measurement of paravalvular leakage. The method of measurement of paravalvular leak rate does not alter the test conditions of the specimen. The location of the valve/substrate test sections on the base plate of the pulse chamber allow the droplets to fall in a near downward path, taking advantage of gravity, to aid in the ease of collection. The unobstructed field of the test sections provide a means of video recording the fluid motion and droplet formations beyond the valve/substrate boundary to aid in the examination of the sewing ring interface through high speed photography and evaluation of the fluid mode change during elevated levels of pulse chamber pressure or pulse rate. And, the system provides a means of rapid screening of prototypes through direct comparison when tested in the same system.

Although this invention has been shown and described with respect to detailed embodiments thereof, it will be understood by those skilled in the art that various changes in form and detail thereof may be made without departing from the spirit and scope of the claimed invention.

I claim:

1. An apparatus for testing paravalvular leakage, comprising:

a pulse chamber pressure vessel having a top, a bottom, at least one side, an interior volume, an inlet and an outlet;

at least one valve mounting opening in the bottom of the pulse chamber pressure vessel, the valve mounting opening in fluid communication with the interior volume;

a flexible valve ring mounting member mounted about each valve mounting opening for mounting a sewing ring of a prosthetic heart valve thereto, said mounting member being an annular member having a central opening for receiving at least part of the prosthetic heart valve, wherein the prosthetic heart valve contains movable elements;

a pulsatile pump, having an inlet and an outlet, wherein the pump outlet is fluidly connected to the inlet of the pulse chamber pressure vessel, and the inlet of the pump is fluidly connected to the outlet of the pulse chamber pressure vessel; and, a drip collection chamber vessel having an inlet and an outlet, the drip collection chamber vessel in fluid communication with each prosthetic heart valve to collect paravalvular leakage.

2. The apparatus of claim 1, wherein the pulsatile pump comprises controls for adjusting stroke volume, discharge pressure, and cyclic rate.

3. The apparatus of claim 1, wherein the pulsatile pump is a piston pump.

4. The apparatus of claim 1, additionally comprising a fixture for receiving the prosthetic heart valve and for constraining the moveable elements of the prosthetic heart valve.

5. The apparatus of claim 1, additionally comprising a fluid reservoir, said fluid reservoir in fluid communication with the outlet of the drip collection chamber pressure vessel, the outlet of the pulse chamber vessel, and the inlet of the pulsatile pump.

6. The apparatus of claim 5, additionally comprising a return pump, the return pump having an inlet in fluid communication with the outlet of the drip collection pressure vessel, and an outlet in fluid communication with the inlet of the fluid reservoir.

7. The apparatus of claim 1, additionally comprising a heater and a temperature controller mounted to the fluid reservoir for controlling the temperature of a circulating fluid in the apparatus.

8. The apparatus of claim 1, additionally comprising a temperature transducer and a pressure transducer mounted to the pulse chamber pressure vessel for detecting the temperature and pressure of fluid in the pulse chamber pressure vessel.

9. The apparatus of claim 1, wherein the drip collection chamber vessel comprises at least one separate collection compartment for each prosthetic heart valve.

10. The apparatus of claim 9, additionally comprising a flow meter connected to each compartment.

11. A method of measuring paravalvular leakage from a prosthetic heart valve, comprising:
providing a prosthetic heart valve, said prosthetic heart valve having a peripheral sewing ring, a frame and moveable elements;
providing a paravalvular leak tester, the leak tester comprising:
a pulse chamber pressure vessel having a top, a bottom, at least one side, an interior volume, an inlet and an outlet;
at least one valve mounting opening in the bottom of the pulse chamber pressure vessel, the mounting member in fluid communication with the interior volume;
a flexible valve ring mounting member mounted about each valve mounting opening for mounting the sewing ring of the prosthetic heart valve thereto, said mounting member being an annular member having a central opening for receiving at least part of the prosthetic heart valve;
a pulsatile pump, having an inlet and an outlet, wherein the pump outlet is fluidly connected to the inlet of the pulse chamber pressure vessel, and the inlet of the pump is fluidly connected to the outlet of the pulse chamber vessel; and,
a drip collection chamber pressure vessel having an inlet and an outlet, the drip collection chamber pressure vessel in fluid communication with each prosthetic heart valve to collect paravalvular leakage.

12. The method of claim 11, wherein the pulsatile pump comprises controls for adjusting stroke volume, discharge pressure, and cyclic rate.

13. The method of claim 11, wherein the pulsatile pump is a piston pump.

14. The method of claim 11, additionally comprising a fixture for receiving the prosthetic heart valve and for constraining the moveable elements of the heart prosthetic valve.

15. The method of claim 11 additionally comprising a fluid reservoir, said fluid reservoir in fluid communication with the outlet of the drip collection chamber vessel, the outlet of the pulse chamber pressure vessel, and the inlet of the pulsatile pump.

16. The method of claim 11 additionally comprising a heater and a temperature controller mounted to the fluid reservoir for controlling the temperature of a circulating fluid in the apparatus.

17. The method of claim 16, additionally comprising a return pump, the return pump having an inlet in fluid communication with the outlet of the drip collection pressure vessel, and an outlet in fluid communication with the inlet of the fluid reservoir.

18. The method of claim 11 additionally comprising a temperature transducer and a pressure transducer mounted to the pulse pressure vessel chamber for detecting the temperature and pressure of fluid in the pulse chamber pressure vessel.

19. The method of claim 11, wherein the drip collection chamber vessel comprises at least one separate collection compartment for each prosthetic heart valve.

20. The method of claim 19, additionally comprising a flow meter connected to each compartment.

21. A method of measuring paravalvular leakage from a prosthetic heart valve, comprising:
providing a prosthetic heart valve, said heart valve having a peripheral sewing ring, a frame and moveable elements;
providing a paravalvular leak tester, the leak tester comprising:
a pulse chamber pressure vessel having a top, a bottom, at least one side, an interior volume, an inlet and an outlet;
at least one valve mounting opening in the bottom of the pulse chamber pressure vessel, the valve mounting opening in fluid communication with the interior volume;
a flexible valve ring mounting member mounted about each valve mounting opening for mounting a sewing ring of a prosthetic heart valve thereto, said mounting member being an annular member having a central opening for receiving at least part of the prosthetic heart valve;
a pulsatile pump, having an inlet and an outlet, wherein the pump outlet is fluidly connected to the inlet of the pulse chamber pressure vessel, and the inlet of the pump is fluidly connected to the outlet of the pulse chamber vessel; and,
a drip collection chamber pressure vessel having an inlet and an outlet, the drip collection chamber pressure vessel in fluid communication with each prosthetic heart valve to collect paravalvular leakage;
mounting the sewing ring of the prosthetic heart valve to the mounting member using at least one mechanical fixation device, such that the moveable elements are restrained from movement, and fluid is blocked from moving through the frame;
filling the apparatus with a fluid;
engaging the pulsatile pump to cause pressurized fluid to flow cyclically into the pulse chamber pressure vessel; and,
measuring paravalvular leakage flowing out from the prosthetic heart valve.

* * * * *